United States Patent [19]
Clear et al.

[11] Patent Number: 5,690,627
[45] Date of Patent: Nov. 25, 1997

[54] ABSORBENT ARTICLE WITH FIT ENHANCEMENT SYSTEM

[75] Inventors: Sandra Hintz Clear, Longwood, Fla.; Kenneth Barclay Buell, Cincinnati; Denise Marie Stelljes, West Chester, both of Ohio; Merlene Adams Cummins, Lakeside Park, Ky.

[73] Assignee: The Procter & Gamble Company, Cincinnati, Ohio

[21] Appl. No.: 730,169

[22] Filed: Oct. 15, 1996

Related U.S. Application Data

[63] Continuation of Ser. No. 357,484, Dec. 16, 1994, abandoned, which is a continuation-in-part of Ser. No. 668,073, Jun. 19, 1996, which is a division of Ser. No. 466,952, Jun. 6, 1995, which is a division of Ser. No. 78,538, Jun. 17, 1993, Pat. No. 5,499,978, which is a continuation of Ser. No. 914,958, Jul. 16, 1992, Pat. No. 5,221,274, which is a continuation of Ser. No. 750,775, Aug. 22, 1991, Pat. No. 5,151,092.

[51] Int. Cl.⁶ ............................................. A61F 13/15
[52] U.S. Cl. ............................................. 604/385.2
[58] Field of Search ........................... 604/385.2, 387

[56] References Cited

U.S. PATENT DOCUMENTS

| | | | |
|---|---|---|---|
| 2,019,835 | 11/1935 | Voss | 604/385.2 |
| 2,731,014 | 1/1956 | Hollingsworth | 604/385.2 |
| 2,798,489 | 7/1957 | Behrman | 604/385.2 |
| 4,050,462 | 9/1977 | Woon et al. | 128/287 |
| 4,205,679 | 6/1980 | Repke et al. | 128/287 |
| 4,578,073 | 3/1986 | Dysart et al. | 604/397 |
| 4,655,760 | 4/1987 | Morman et al. | 604/385 |
| 4,704,114 | 11/1987 | Wilson et al. | 604/385.2 |
| 4,753,648 | 6/1988 | Jackson | 604/389 |
| 4,857,067 | 8/1989 | Wood et al. | 604/389 |
| 4,891,258 | 1/1990 | Fahrenkrug | 428/138 |
| 4,917,682 | 4/1990 | Lancaster et al. | 604/385.2 |
| 5,151,092 | 9/1992 | Buell et al. | 604/385.2 |
| 5,221,274 | 6/1993 | Buell et al. | 604/385.2 |
| 5,269,775 | 12/1993 | Freeland et al. | 604/385.2 |
| 5,358,500 | 10/1994 | Lavon et al. | 604/385.2 |
| 5,389,095 | 2/1995 | Suzuki et al. | 604/385.2 |
| 5,470,639 | 11/1995 | Gessner et al. | 604/385.2 |

FOREIGN PATENT DOCUMENTS

| | | |
|---|---|---|
| 0 215 408 A2 | 3/1987 | European Pat. Off. . |
| 0 359 410 A1 | 3/1990 | European Pat. Off. . |
| WO93/01785 | 2/1993 | WIPO . |
| WO 93/17648 | 9/1993 | WIPO . |
| WO 95/22951 | 8/1995 | WIPO . |

*Primary Examiner*—Michael J. Milano
*Attorney, Agent, or Firm*—Edward J. Milbrada; Steven W. Miller; Jeffrey V. Bamber

[57] ABSTRACT

Absorbent articles, such as disposable diapers, incontinence briefs, diaper holders, training pants, and the like having fit panels that improve body contact of the containment assembly, with resulting improved fit, are provided. The fit panels have longitudinal elastic extensibility that provides a body contact force causing the containment assembly to have improved contact with a wearer throughout the full range of wearer motions. The longitudinal elastic extensibility of the fit panel also allows the absorbent article to adapt to the change in body rise dimensions that occurs during normal movement. An alternative embodiment of the invention also provides a stretchable attachment component allowing the waist feature of the absorbent article to be attached to the waistband of a wearer's clothing in a manner such that it can stretch and contract with the waistband while remaining attached.

23 Claims, 4 Drawing Sheets

ABSORBENT ARTICLE WITH FIT ENHANCEMENT SYSTEM

This is a continuation of application Ser. No. 08/357,484 filed on Dec. 16, 1994 now abandoned; which is a continuation-in-part of application Ser. No. 08/668,073, filed on Jun. 19, 1996; which is a divisional of application Ser. No. 08/466,952, filed on Jun. 6, 1995; which is a divisional of application Ser. No. 08/078,538, filed on Jun. 17, 1993 now U.S. Pat. No. 5,499,978; which is a continuation of application Ser. No. 07/914,958, filed on Jul. 16, 1992, now U.S. Pat. No. 5,221,274; which is a continuation of application Ser. No. 07/750,775, filed on Aug. 22, 1991, now U.S. Pat. No. 5,151,092.

FIELD OF INVENTION

The present invention relates to absorbent articles such as diapers, incontinence briefs, diaper holders, training pants and the like and, more particularly, to providing the absorbent article with fit panels with longitudinal elastic extensibility for improved fit.

BACKGROUND OF THE INVENTION

Infants and other incontinent individuals wear absorbent articles such as diapers to receive and contain urine and other body exudates. Absorbent articles function both to contain discharged materials and to isolate the materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967 describes the first disposable diaper to achieve broad acceptance and commercial success.

However, the absorbent articles currently available to the public fail to completely meet consumer needs for leakage control, aesthetically pleasing fit, and the ability for an article to maintain fit throughout the full range of wearer motions.

There have been many attempts in the prior art to provide disposable absorbent articles to better meet these needs. For example U.S. Pat. No. 3,860,003, entitled "Contractible Side Portions for Disposable Diaper" issued to Buell on Jan. 14, 1975 describes a diaper with thin, flexible side portions elasticized to provide improved leakage control and leg fit. Such diapers have enjoyed wide commercial success. Further, U.S. Pat. No. 4,476,709, entitled "Form-Fitting Self-Adjusting Disposable Garment with a 3-Section Stretchable Outer Cover" issued to Stevens on Jul. 11, 1988 discloses diapers with a three section, resiliently stretchable outer cover. Finally, U.S. Pat. No. 5,269,775, entitled "Trisection Topsheets for Disposable Absorbent Articles and Disposable Articles Having Such Trisection Topsheet" issued to Freeland, et al. on Dec. 14, 1993 discloses diaper topsheets divided into three sections some of which have elastic extensibility. Still, the need for absorbent articles with improved fit and leakage control exists.

In addition the catamenial art also teaches stretchable absorbent articles. For example, U.S. Pat. No. 4,753,648, entitled "Sanitary Napkin Adhesively Attached Via Elastic Member" issued to Jackson on Jun. 28, 1988 describes a central absorbent with one or more elastic members attached and adhesive tabs disposed on the elastic members. Also, commonly assigned international application WO 93/01785, entitled "Stretchable Absorbent Articles" which was published on Feb. 4, 1993 discloses thin sanitary napkins that are stretchable, especially in the longitudinal direction.

However, the art is silent on absorbent articles of simple construction having both longitudinally and laterally elastic functionality in the same article.

Thus, it would be advantageous to provide absorbent articles having features that provide better fit, reduced leakage, and wearer comfort. It would be further advantageous to provide an absorbent article which has improved contact with the body of a wearer. It would be particularly useful if the absorbent article could fit a wider range of body rise dimensions than previously described absorbent articles. For example, the body rise dimension of a typical infant changes by between two and three inches as the infant moves from a standing to a sitting position. This change can cause gapping with resulting leakage. Additionally, it would be advantageous to provide absorbent articles that can be worn under clothing and absorbent articles that can be attached to such clothing.

Therefore, it is an object of the present invention to provide absorbent articles having improved fit and containment for the wearer during use.

It is a further object of the present invention to provide absorbent articles with fit panels having longitudinally oriented elastic extensibility that sustains body contact for the containment assembly of the article and widens the range of body rise dimensions the article will fit.

It is still a further object of the invention to provide absorbent articles with both fit panels and an elasticized waist feature that can expand and contract in unison with dimensional changes due to wearer movement.

It is an additional object of the invention to provide absorbent articles with a clothing attachment system that allows the article to be attached to some portion of a wearer's clothing and remain firmly attached as the wearer's clothing expands and contracts.

These and other objectives of the present invention will be more readily apparent when considered in reference to the following description and when taken in conjunction with the accompanying drawings.

SUMMARY OF THE INVENTION

The present invention provides absorbent articles such as disposable diapers, incontinent briefs, diaper holders, training pants and the like that have elastically extensible fit panels and elastic waist features that provide improved fit for a variety of body dimensions. Such absorbent articles comprise a containment assembly generally comprising a liquid pervious topsheet, a liquid impervious backsheet, an absorbent core disposed between the topsheet and the backsheet; elasticized leg cuffs; fit panels having longitudinally oriented elastic extensibility; an elastic waist feature; and a fastening system.

The fit panels are elastically extensible in at least the longitudinal direction. A fit panel extends longitudinally outward from at least one end edge of the containment assembly and preferably joins with the elastic waist feature. Such fit panels preferably extend the full transverse width of the absorbent article. The longitudinal elastic extensibility of a fit panel provides a body contact force that improves the fit of the absorbent article by better insuring the containment assembly remains in body contact throughout the full range of a wearer's motions. Additionally, since the absorbent article is elastically extensible in the longitudinal direction it can fit a wider range of body rise dimensions than other absorbent articles known to the art. In a preferred embodiment of the present invention, the absorbent article has a fit panel extending from each end edge of the containment assembly. The fit panels preferably comprise portions of the topsheet and the backsheet that have been mechanically stretched and joined to an intermediate elastic member to form a "zero strain stretch laminate". Also, by using a "zero strain stretch laminate" comprising the topsheet, an elastic member, and the backsheet to provide longitudinal elastic extensibility to the absorbent article, the structure of the article is of simpler construction than articles of the prior art where it was necessary to provide means for allowing the containment assembly to "float" inside an outer cover that possesses longitudinal stretch.

The elastic waist feature provides transverse direction elastic extensibility to the absorbent article. The elastic waist feature preferably extends longitudinally outwardly from the waist edge of at least one fit panel to the waist edge of the absorbent article. The transverse direction elastic extensibility allows the absorbent article to respond to dimensional changes about the waist of a wearer thereby reducing sagging and gapping. As discussed hereinabove regarding fit panels, a preferred embodiment of the waist feature of the present invention comprises a "zero strain stretch laminate" of the topsheet, the backsheet and an elastic member to provide the transverse direction elastic extensibility.

An additional embodiment of the present invention is an absorbent insert having a clothing attachment system in place of the fastening system. The clothing attachment system can comprise an adhesive patch, a mechanical fastener, or, preferably, a stretchable hot melt adhesive, most preferably an elastically extensible hot melt adhesive, slot extruded to cover at least 25% of the surface area of the elastic waist feature.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded alter a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, training pants, and the like.

Figure 1:
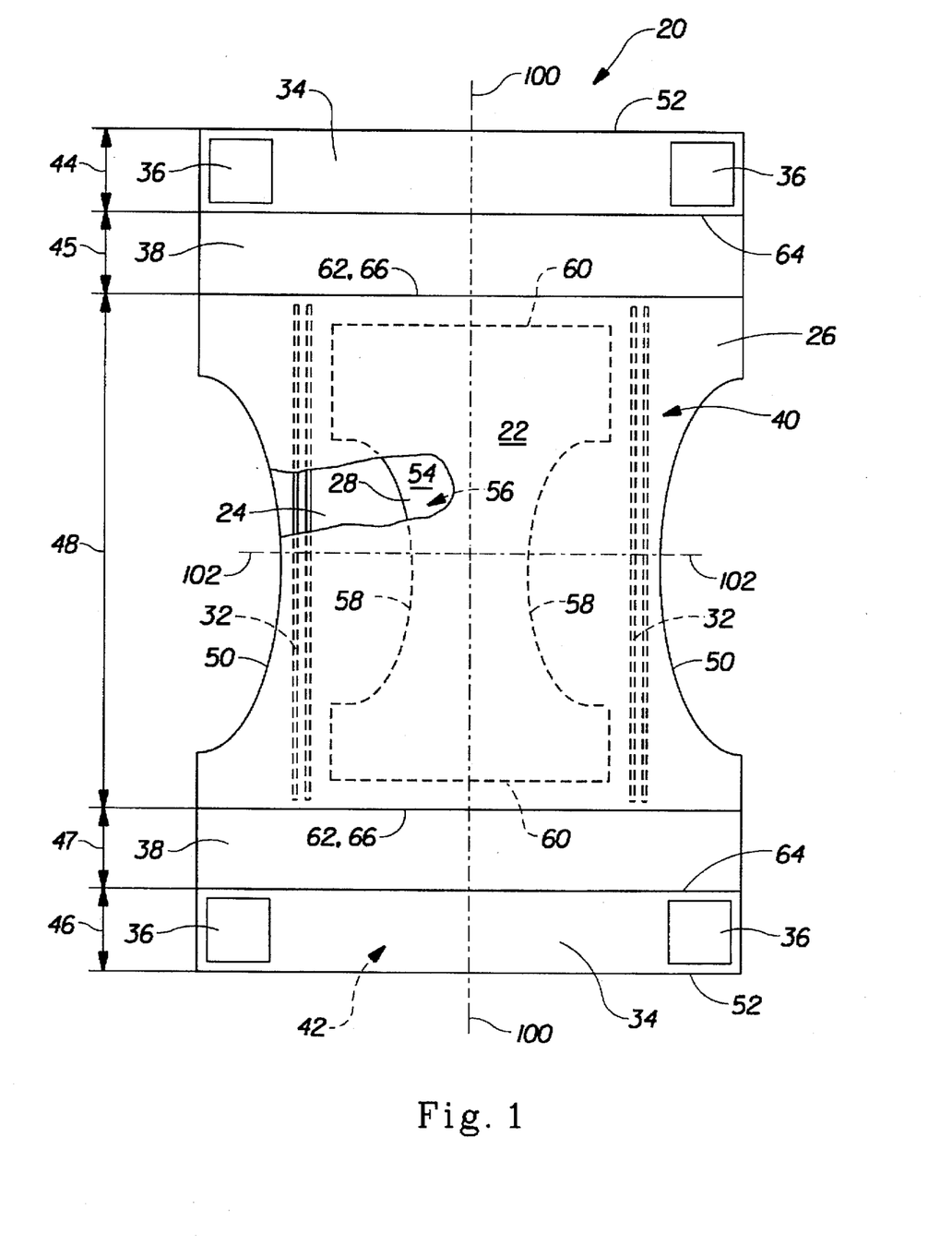
FIG. 1 is a plan view of a disposable diaper embodiment of the present invention having portions cut-away to reveal the underlying structure, and with the outer surface of the diaper facing the viewer.

FIG. 1 is a plan view of the diaper 20 of the present invention in its flat-out, uncontracted state (i.e., with elastically induced contraction pulled out) with portions of the structure being cut-away to more clearly show the construction of the diaper 20 and with the portion of the diaper 20 which faces away from the wearer, the outer surface 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The diaper preferably further comprises elasticized leg cuffs 32; an elastic waist feature 34; a fastening system 36; and fit panels 38.

The diaper 20 also has two centerlines, a longitudinal centerline 100 and a transverse centerline 102. The term "longitudinal", as used herein, refers to a line, axis, or direction in the plane of the diaper 20 that is generally aligned with (i.e. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (i.e. divides the wearer into front and back body halves).

The diaper 20 is shown in FIG. 1 to have an outer surface 40 (facing the viewer in FIG. 1), an inner surface 42 opposed to the outer surface 40, a crotch region 48 centered approximately at the intersection of the longitudinal centerline 100 and the transverse centerline 102, a rear fit region 45 and a front fit region 47 each extending longitudinally outwardly from one end of the crotch region 48, a front waist region 46 and a rear waist region 44 extending longitudinally outwardly from the front fit region 47 and the rear fit region 45 respectively, and a periphery which is defined by the outer perimeter or edges of the diaper 20 in which the longitudinal edges are designated 50 and the end edges are designated 52. The inner surface 42 of the diaper 20 comprises that portion of the diaper 20 which is positioned adjacent to the wearer's body during use (i.e., the inner surface 42 generally is formed by at least a portion of the topsheet 24 and other components joined to the topsheet 24). The outer surface 40 comprises that portion of the diaper 20 which is positioned away from the wearer's body (i.e., the outer surface 40 is generally formed by at least a portion of the backsheet 26 and other components joined to the backsheet 26). As used herein, the term "joined" encompasses configurations whereby an element is directly secured to another element by affixing the element directly to the other element, and configurations whereby the element is indirectly secured to the other element by affixing the element to an intermediate member(s) which in turn is affixed to the other element. The rear waist region 44 and the front waist region 46 preferably extend from the end edges 52 of the diaper 20 to the rear fit region 45 and the front fit region 47 respectively. The rear fit region 45 extends from the rear waist region 44 to the crotch region 48 and the front fit region 47 extends from the front waist region 46 to the crotch region 48.

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. Thus, the containment assembly 22 for the diaper 20 preferably comprises the topsheet 24, the backsheet 26, and the absorbent core 28. Also, as shown in FIG. 1, the containment assembly 22 has end edges 62 defined by the intersection of the crotch region 48 and the fit regions 45 or 47 of the diaper 20.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; and U.S. patent application Ser. No. 08/155,406 entitled "Absorbent Article with a Structural Elastic Like Film Web Waist Belt" which was filed by Donald C. Roe on Nov. 19, 1993; each of which is incorporated herein by reference.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side 54, a body-facing side 56, a pair of side edges designated 58, and a pair of waist edges designated 60. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; fluid stable aggregates of superabsorbent polymers; or any equivalent material or combinations of materials.

The configuration and construction of the absorbent core 28 may widely vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

Exemplary absorbent structures for use as the absorbent core 28 of the present invention that have achieved wide acceptance and commercial success are described in U.S. Pat. No. 4,610,678 entitled "High-Density Absorbent Structures" issued to Weisman, et al. on Sep. 9, 1986; U.S. Pat. No. 4,673,402 entitled "Absorbent Articles With Dual-Layered Cores" issued to Weisman, et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany, et al. on May 30, 1989. The absorbent core may further comprise the dual core system containing an acquisition/distribution core of chemically stiffened fibers positioned over an absorbent storage core as detailed in U.S. Pat. No. 5,147,345, entitled "High Efficiency Absorbent Articles For Incontinence Management" issued to Young, et al. on Sep. 15, 1992. Additionally, the absorbent core may comprise the porous, absorbent, polymeric macrostructures discussed in U.S. Pat. No. 5,102,597 entitled "Porous, Absorbent, Polymeric Macrostructures and Methods of Making the Same" issued to Roe, et al. on Apr. 7, 1992. A preferred structure for the absorbent core 28 is described in U.S. Pat. No. 5,234,423, entitled "Absorbent Article With Elastic Waist Feature and Enhanced Absorbency" issued to Alemany, et al., on Aug. 10, 1993. Each of these patents is incorporated herein by reference.

The backsheet 26 is positioned adjacent the garment-facing surface 54 of the absorbent core 28 and is preferably joined thereto by attachment means such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola, et al. on Mar. 4, 1986. A preferred attachment means comprises several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments, however, the backsheet 26 may permit vapors to escape from the absorbent core 28 (i.e., the backsheet is breathable). Thus, the backsheet 26 may comprise a woven or nonwoven material, polymeric films such as thermoplastic films of polyethylene or polypropylene, or composite materials such as a film-coated nonwoven material. A suitable backsheet 26 is a thermoplastic film having a thickness of from about 0.012 mm (0.5 mil) to about 0.051 mm (2 mils). Preferably, the backsheet 26 is embossed and/or matte finished to provide a more clothlike appearance.

In preferred embodiments of the present invention, at least a portion of the backsheet 26 is subjected to mechanical stretching in order to provide a "zero strain" stretch laminate for the fit panels 38 and the elastic waist feature 34. The backsheet 26 can be stretched by directing the backsheet through an incremental mechanical stretching system similar to the operation described with respect to the formation of the "zero strain" stretch laminates in U.S. Pat. No. 5,151,092 entitled "Absorbent Article With Dynamic Elastic Waist Feature Having A Predisposed Resilient Flexural Hinge", issued to Buell, et al., on Sep. 29, 1992. Accordingly, the backsheet 26 is preferably elongatable, more preferably drawable, but not necessarily elastomeric, so that the backsheet 26 will, upon mechanical stretching, be at least to a degree permanently elongated such that it will not fully return to its original undistorted configuration. In preferred embodiments, the backsheet 26 can be subjected to mechanical stretching without undue rupturing or tearing. Thus, it is preferred that the backsheet 26 have an ultimate elongation to break of at least 400% to about 700% in the cross-machine direction as measured using a method consistent with ASTM (American Society for Testing Materials) D-638. Films suitable for use as the backsheet 26 generally contain a high content of linear low density polyethylene. A suitable material for the backsheet 26 is RR8220 blown film as manufactured by Tredegar Industries, Inc. of Terre Haute, Ind.

The size of the backsheet 26 is dictated by the size of the absorbent core 28 and the exact diaper design selected. In a preferred embodiment, the backsheet 26 has a modified hourglass shape extending beyond the absorbent core a minimum distance of about 1.3 cm to about 2.5 cm (about 0.5 to about 1.0 inch) around the entire diaper periphery.

The topsheet 24 is positioned adjacent the body-facing surface 56 of the absorbent core 28 and is preferably joined thereto and to the backsheet 26 by attachment means such as those well known in the art. Suitable attachment means are described hereinabove with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is preferably liquid pervious, permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of the present invention, at least a portion of the topsheet 24 is subjected to mechanical stretching in order to provide a "zero strain" stretch laminate that forms the elastic waist feature 34 and the fit panels 38. The topsheet 24 can be stretched by any methods as are known in the art including, but not limited to, the methods described herein with respect to the formation of a "zero strain" stretch laminate. Thus, the topsheet 24 is preferably elongatable, more preferably drawable, but not necessarily elastomeric, so that the topsheet 24 will, upon mechanical stretching, be at least to a degree permanently elongated such that it will not fully return to its original configuration. In preferred embodiments, the topsheet 24 can be subjected to mechanical stretching without undue rupture or tearing. Thus, it is preferred that the topsheet 24 have a low yield strength and a high elongation to break.

There are a number of manufacturing techniques which may be used to manufacture the topsheet 24. For example, the topsheet 24 may be a nonwoven web of fibers. When the topsheet 24 comprises a nonwoven web, the web may be spunbonded, carded, wet-laid, melt-blown, hydroentangled, combinations of the above, or the like. A suitable topsheet 24 is a spunbonded nonwoven fabric which is manufactured by PolyBond Inc. of Waynesboro, Va. and is known as Wettable Polyethylene Spunlaid 30434.

The diaper 20 preferably further comprises elasticized leg cuffs 32 for providing improved containment of liquids and other body exudates. Each elasticized leg cuff 32 may comprise one of several different embodiments for reducing the leakage of body exudates in the leg regions. (The leg cuffs can be and are sometimes also referred to as leg bands, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz, et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described hereinabove, each elasticized leg cuff 32 preferably comprises the dual cuffs as described in the above-referenced U.S. Pat. No. 4,695,278.

In a preferred embodiment of the diaper 20, the elasticized leg cuffs 32 are located on both longitudinal sides of the absorbent core 28 between the side edges 58 of the absorbent core 28 and the longitudinal edges 50 of the diaper 20 and extend longitudinally between the end edges 62 of the containment assembly 22. This is not to limit the present invention to embodiments wherein the elasticized leg cuffs 32 only extend between the end edges of the containment assembly. Other embodiments are contemplated wherein the leg cuffs extend longitudinally to the waist edges of the fit panel 64 and beyond to the end edges 52 of the diaper 20. For embodiments wherein the elasticized leg cuffs 32 extend beyond the end edges 62 of the containment assembly 22, it is important that the leg cuff not interfere with the functionality of those features on which elasticized the leg cuff 32 may be disposed. For example a means of providing a leg cuff 32 which extends beyond the end edges 62 of the containment assembly 22 without interfering with the functionality of the fit panel 38 would be to extend the diaper 20 longitudinally, attach the leg cuffs 32 to the extended diaper, and allow the structure to relax to its unextended state. Further, for designs wherein the elasticized leg cuffs 32 extend longitudinally to the waist edges of the fit panel 64, the contribution of the elasticized leg cuff 32 to the body contact force discussed hereinbelow must be considered.

As shown in FIG. 1 the fit panels 38 of the diaper 20 preferably extend longitudinally outwardly from the end edges 62 of the containment assembly 22 to the waist edges of the fit panel 64 and transversely between the longitudinal edges 50 of the diaper 20 (As used herein, the term "waist edge of the fit panel" refers to that line, which is parallel to the transverse centerline 102 of the diaper 20, that defines the longitudinal extent of elastic extensibility having a longitudinal vector component in the diaper 20 as measured from the end edge 62 of the containment assembly 22). In this preferred embodiment, the chassis edge 66 of the fit panel 38 is joined to the end edge 62 of the containment assembly 22 and the fit panel extends longitudinally outwardly to the waist edge of the fit panel 64. However, as long as the fit panels 38 are longitudinally located somewhere between the end edges 62 of the containment assembly 22 and the waist edges of the fit panel 64 they are considered to be within the scope of the present invention. These fit panels 38 provide the body contact force that keeps the containment assembly 22 in close body contact throughout the expected range of movements of a wearer. The longitudinally oriented elastic extensibility that gives rise to the body contact force also enables the diaper 20 to fit a wider range of "body rise dimensions" than diapers of the prior art (As used herein the term "body rise dimension" refers to the measured distance on a wearer beginning at the navel, extending through the crotch and ending at the small of the back). A diaper of the present invention can consist of one or more longitudinally extending fit panels. Further, while a fit panel 38 or any of its constituent elements can comprise a separate element affixed to the containment assembly 22, the fit panels 38 are preferably constructed as an extension of other elements of the diaper such as the backsheet 26 or the topsheet 24, more preferably both the backsheet 26 and the topsheet 24.

Preferred embodiments of the present invention are constructed so as to have two fit panels 38, one positioned in the rear fit region 45 and one positioned in the front fit region 47. The elastic extensibility of the fit panel in the rear fit region 45 is preferably at least equal to the elastic extensibility of the fit panel in the front fit region 47. In a preferred embodiment of the present invention, the elastic extensibility of the fit panel in the rear fit region 45 is greater than the elastic extensibility of the fit panel in the front fit region 47. More preferably, the elastic extensibility of the fit panel in the rear fit region 45 is approximately 1.5 to 2 times the elastic extensibility of the fit panel in the front fit region 47. As used herein the term "elastic extensibility" refers to the amount a fit panel 38 can be stretched while it still remains elastically extensible, as described below. For example, a fit panel in the rear fit region 45 that is 1.5 to 2 times the longitudinal length of a fit panel in the front fit region 47 would have 1.5 to 2 times the elastic extensibility of the fit panel in the front fit region 47. Alternatively, different degrees of elastic extensibility could be achieved by using materials with different moduli of elasticity.

The fit panels 38 may comprise any suitable elastically extensible materials. As used herein, the term "elastically extensible" refers to materials that extend in at least one direction when a force is applied to the material, and return to approximately their original dimensions after the force is released. This elastic extensibility can have either only a longitudinal vector component or both longitudinal and lateral vector components (depending on the orientation of the applied force) so as to provide longitudinal extensibility.

Preferably, a fit panel 38 of the present invention is elastically extensible from about 1 cm (0.25 inch) to about 2.5 cm (1 inch) without rupture and more preferably from about 1 cm (0.25 inch) to about 5 cm (2 inches) without rupture, although a fit panel 38 which has a lesser elongation without rupture, such as from about 1 cm (0.25) inch to about 2 cm (0.75 inch) is suitable. As used herein, the term "rupture" means tearing, fracturing, or breaking into two or more subparts. This property provides for conformance to the shape of the wearer's body and maintenance of close contact to the skin of the wearer. Also, a diaper 20 with a fit panel 38 which is relatively highly extensible can comfortably fit a larger range of body rise dimensions.

To prevent excessive forces from being exerted against a wearer's body when the diaper 20 is stretched about the body of the wearer, the fit panel 38 preferably has a body contact force of less than about 200 grams (0.45 pounds) upon elongation from about 0.25 cm (0.1 inch) to about 5 cm (2 inches). As used herein, the term "body contact force" refers to the highest reading obtained on a tensile machine when a sample of the fit panel 38 is pulled throughout the specified range of elongation as described herein. More preferably, the fit panel 38 has a body contact force less than about 175 grams (0.39 pounds) when elongated from about 0.25 cm (0.1 inch) to about 5 cm (2 inches) and even more preferably, a body contact force of less than about 100 grams (0.22 pounds) when elongated from about 0.25 cm (0.1 inch) to about 5 cm (2 inches). The gage length is taken parallel to the principal axis of elongation, if the sample is orthotropic or anisotropic.

Body contact force may be measured using an Instron Model 1122 tensile machine made by the Instron Corporation of Canton, Mass. utilizing constant rate of elongation cross heads traveling at a separation speed of about 50.8 centimeters per minute (20 inches per minute). A fit panel 38 is removed from the diaper 20 insuring there is sufficient material at each end of the fit panel so the entire panel can contribute to the measured body contact force (i.e. insure that there is roughly 2 cm (0.75 inch) of material extending from each end of the fit panel that can be inserted into the jaws of the tensile machine). Set the gauge length of the tensile machine such that it equals the free longitudinal length of the fit panel 38 (about 5 cm or 2 inches for a medium diaper). Use jaws with sufficient width that the force to elongate the entire fit panel 38 can be measured (about 10 cm or 4 inches for a medium diaper). The sample is placed in the tensile machine and elongated, in tension, until a reading of about 200 grams is obtained. The resulting elongation at such a load is then noted.

All elongation readings should preferably be taken within about 5 seconds of reaching the desired elongation. A strip chart recorder may advantageously be utilized to obtain the readings which occur when the sample reaches the desired tension.

The sustainable body contact force of the fit panel 38 on the wearer is also an important property of the fit panel. This can be measured by stress relaxation. As used herein, the term "stress relaxation" refers to the dissipation and diminution of stresses and the associated contractive and restoring forces which occur over time when a sample is elongated from its free length. Stress relaxation may be enhanced by application of heat or may occur due to elongation of the fit panel 38 to a range which causes slip of the molecular structure to occur. It is desired that the stress relaxation occur after a relatively short period of time from initial elongation of the fit panel 38 so that the wearer does not experience discomfort caused by high contractive forces of the fit panel 38 for an undue length of time. On the other hand, it is necessary that the fit panel maintain a minimum body contact force over time to prevent bagging with resulting leakage. A fit panel 38 which exhibits a body contact force of less than about 50 grams and greater than 10 grams, when tested as described hereinabove, after a period of at least about 10 minutes at a temperature of at least about 22° C. when elongated to a range of about 1 cm (0.25 inch) to about 5 cm (2 inch) is suitable. The body contact force is preferably less than about 25 grams throughout the entire range of elongation after being elongated for at least 10 minutes.

Examples of materials suitable for use as a fit panel 38 include, for example, elastically extensible laminates preferably comprising the topsheet 24 and the backsheet 26. In an especially preferred embodiment, at least a portion of the topsheet 24 and the backsheet 26 are joined to an elastic member (A particularly preferred elastic member will comprise an elastically extensible adhesive film such as Findley adhesive 198-338 supplied by Findley Adhesives of Wauwatosa, Wis.) and subjected to mechanical stretching in order to provide a "zero strain" stretch laminate extensible in at least one direction. This elastic extensibility allows the fit panels to expand and contract in conjunction with the motions of the wearer and reduces the possibility of red marks in the regions where the fit panels contact the wearer. Examples of suitable methods for mechanically stretching the material forming the fit panels are described in the above referenced U.S. Pat. No. 5,151,092 issued to Buell, et al. which is incorporated herein by reference.

Alternatively, the fit panel 38 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the copending, commonly assigned U.S. patent application Ser. No. 08/203,456 entitled "Absorbent Article with Multiple Zone Structural Elastic-Like Film Web Extensible Waist Feature" filed by Donald C. Roe, et al. on Feb. 24, 1994, which is incorporated herein by reference.

The diaper 20 preferably further comprises an elastic waist feature 34 that helps provide improved fit and containment. The elastic waist feature 34 is that portion or zone of the diaper 20 which is intended to elastically expand and contract to dynamically fit the wearer's waist. The lateral tension of this elastic expansion and contraction provides not only for dynamic fit of a wearer's waist but also helps create a seal around that waist with resulting reduction in leakage of bodily exudates at the waist. The elastic waist feature 34 preferably extends longitudinally outwardly from at least one of the waist edges 64 of the fit panels 38 and generally forms at least a portion of the end edge 52 of the diaper 20. Disposable diapers are generally constructed so as to have two waist features, one positioned in the rear waist region 44 and one positioned in the front waist region 46, although diapers can be constructed with a single waist feature. Further, while the elastic waist feature 34 or any of its constituent elements can comprise a separate element affixed to the diaper 20, the elastic waist feature 34 preferably is constructed as an extension of other elements of the diaper such as the backsheet 26, the topsheet 24, or more preferably both the backsheet 26 and the topsheet 24.

The elastic waist feature 34 may comprise any suitable elastically extensible materials. This elastic extensibility can have either only a lateral vector component or both longitudinal and lateral vector components (depending on the orientation of the applied force) so as to provide lateral extensibility. Suitable materials for use as the elastic waist feature 34 are described hereinabove with respect to the fit panels 38.

The elastic waist feature 34 may be constructed in a number of different configurations including those described in U.S. Pat. No. 4,515,595 entitled "Disposable Diapers with Elastically Contractible Waistbands" issued to Kievit, et al. on May 7, 1985 and the above referenced U.S. Pat. No. 5,151,092 issued to Buell; each of these patents being incorporated herein by reference. Further, the elastic waist feature 34 may comprise "pleats" that may be activated by the diaperer to provide additional extension in the waist regions. (As used herein, the term "pleats" refers to regions of material that have been folded back upon themselves such that when an activation force is applied the material unfolds.) Alternatively, the elastic waist feature 34 may make use of configurations which comprise a SELF web as described in the hereinbefore referenced U. S. patent application Ser. No. 08/203,456 of Roe, et al.

The diaper 20 additionally comprises a fastening system 36. In preferred embodiments of the present invention, the fastening system 36 is designed such that only the soft, non-irritating elements of the diaper and the fastening system will come in contact with the wearer's skin. Such preferred fastening systems also help maintain lateral tension in the elastic waist feature 34.

The fastening system 36 can comprise any attachment means known in the art including pressure sensitive adhesives, cohesive materials, mechanical fasteners, hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" issued to Buell on Nov. 19, 1974; and U.S. Pat. No. 4,662,875 entitled "Absorbent Article" issued to Hirotsu, et al. on May 5, 1987. Exemplary fastening systems comprising mechanical fastening components are described in U.S. Pat. No. 5,058,247 entitled "Mechanical Fastening Prong" issued to Thomas on Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. In a preferred embodiment of the present invention, the fastening system comprises a dual tension fastening system as described in U.S. Pat. No. 5,151,092 entitled "Absorbent Article with Dynamic Elastic Waist Feature Having a Predisposed Resilient Flexural Hinge" issued to Buell, et al. on Sep. 29, 1992. Each of the above-listed patents is incorporated herein by reference.

The diaper 20 is preferably applied to a wearer by positioning the rear waist region 44 under the wearer's back. The remainder of the diaper 20 is then drawn up between the wearer's legs so that the front waist region 46 is positioned across the front of the wearer. In pulling the diaper 20 through the wearer's legs a slight tension is applied to the rear fit panel 45 and the front fit panel 47. The fastening system 36 is then "activated". For example, by releasing a tab portion (not shown) of a tape tab (not shown), tensioning the elastic waist feature 34 by stretching it about the waist of the wearer while still grasping the tab portion and applying the tab portion to a tape attachment surface (not shown). These steps are repeated for the other side of the diaper. If embodiments of the fastening system 36, other than fastening tapes, are used, the fastening system 36 would be "activated" as required by the design of the fastening system 36. The tensioning applied to the rear fit panel 45 and the front fit panel 47 as the diaper 20 is pulled through the wearer's legs provides the body contact force with resulting improved fit.

In an alternative embodiment of the present invention, useful as a training pant or pull on diaper, the longitudinal edges 50 of the diaper 20 in the waist regions 44 and 46 extend laterally outboard of the longitudinal edges 50 in the remaining regions of the diaper. That is, for this alternative embodiment, the diaper is wider in the waist regions 44 and 46 than in other regions. Further, the longitudinal edges in waist regions 44 and 46 are joined rather than being provided with a fastening system. That is, the diaper 20 is folded about its transverse centerline 102 so that the front waist region 46 is opposite the rear waist region 44. The opposed longitudinal edges 50 of the diaper 20 in the front and rear waist regions (44 and 46 respectively) are then joined by means familiar to the art to form side seams. Examples of means of joining the edges are given in U.S. Pat. No. 5,236,430 entitled "Disposable Training Pant Having Fusion Slit Side Seams" issued to Bridges on Aug. 17, 1993 which is incorporated herein by reference. The side seams may be either separable (i.e. the front and rear waist regions can be separated along the seam, if necessary, while remaining essentially intact) or secure (i.e. the front and rear waist regions do not remain essentially intact if they are separated along the seam) depending on the specific design of the absorbent article.

Figure 2:
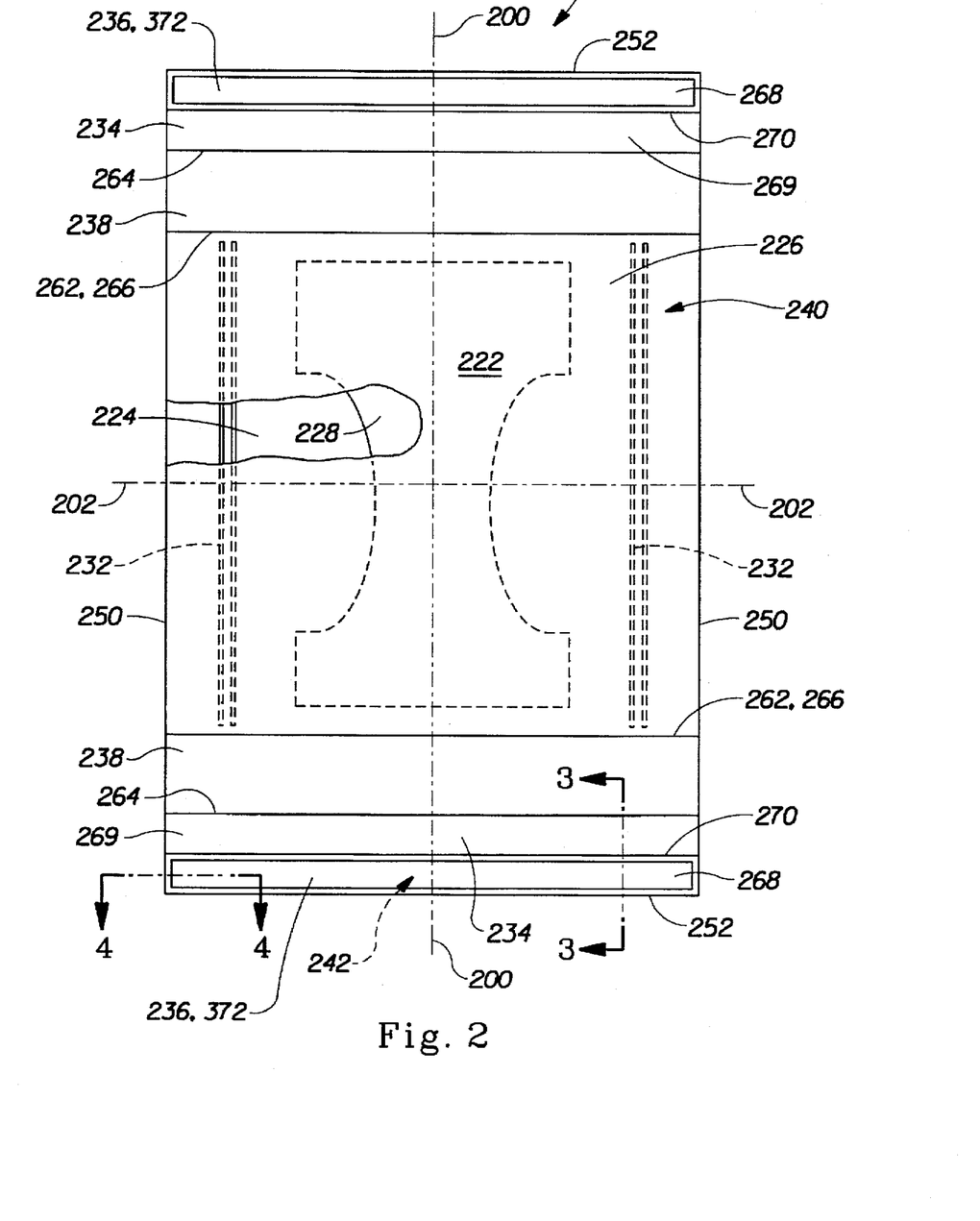
FIG. 2 is a plan view of an alternative embodiment of the present invention comprising an absorbent insert to be placed inside a wearer's underwear with portions of the insert being cut-away to reveal the underlying structure, and with the outer surface of the insert facing the viewer.

FIG. 2 shows a preferred alternative embodiment of the present invention. In this case, the absorbent article is an elasticized insert. Such inserts can be worn under clothing and are particularly useful during toilet training of toddlers and for incontinent adults.

FIG. 2 is a plan view of the insert 220 of the present invention in its flat-out, uncontracted state (i.e., with elastically induced contraction pulled out) with portions of the structure being cut-away to more clearly show the construction of the insert 220 and with the portion of the insert 220 which faces away from the wearer, the outer surface 240, facing the viewer. As shown in FIG. 2, the insert 220 comprises a containment assembly 222 preferably comprising a liquid pervious topsheet 224; a liquid impervious backsheet 226 joined to the topsheet; and an absorbent core 228 positioned between the topsheet 224 and the backsheet 226 and having waist ends 262. The insert preferably further comprises elasticized leg cuffs 232; a waist feature 234; a clothing attachment system 236; and fit panels 238.

The insert 220 as shown in FIG. 2 also has two centerlines, a longitudinal centerline 200 and a transverse centerline 202. In addition, it has an outer surface 240 (facing the viewer in FIG. 2), an inner surface 242 opposed to the outer surface 240, longitudinal sides 250 and end edges 252.

The clothing attachment system 236 is preferably operatively associated with the waist feature 234. The clothing attachment system 236 is located adjacent to both end edges 252 of the insert 220 and is placed on the outer surface 240 of the insert. Depending on the longitudinal length of the insert 220, the clothing attachment system 236 either joins the insert 220 to the body facing side of a wearer's undergarments or folds over the waistband of the undergarment and joins the insert 220 to the garment facing side of the waistband. Preferably, the clothing attachment system 236 folds over the waistband of the undergarment.

If the clothing attachment system 236 folds over the waistband of the undergarment, a fold line 270 can divide the waist feature 234 into two portions. The first portion 268 extends longitudinally toward the transverse centerline 202 from the end edge 252 of the insert 220 to the fold line 270. The second portion 269 extends longitudinally toward the transverse centerline 202 from the fold line 270 to waist edge 264 of the fit panel 238.

One form of the clothing attachment system 236 can comprise an adhesive area as described in U.S. Pat. No. 4,597,760 entitled "Waste-Containment Garment Having Disposable Elasticized Insert" issued to Buell on Jul. 1, 1986 which is incorporated herein by reference. Alternatively, the clothing attachment system 236 can comprise mechanical fastening components such as Velcro® or other hook and loop fastening systems. As used herein, the term "hook fastening material" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary mechanical closure element such as a loop fastening material or another hook fastening material. An example of a hook fastening material suitable for use in the present invention can be found in U.S. Pat. No. 5,058,247 entitled "Mechanical Fastening Prong" issued to Thomas Oct. 22, 1991 which is incorporated herein by reference. When clothing attachment systems such as described hereinabove are used, they are preferably applied in intermittent patterns to allow the waist feature to expand or contract between the application locations.

Figure 3:
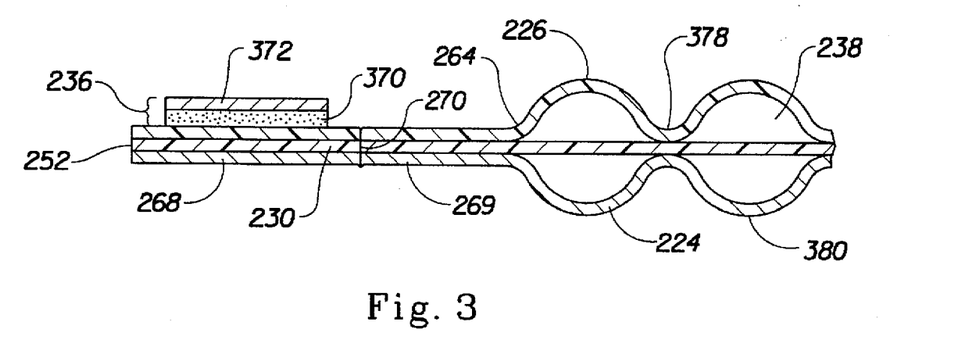
FIG. 3 is a fragmentary sectional view of the absorbent insert of FIG. 2 taken along section line 3—3 of FIG. 2.

A particularly preferred embodiment of the clothing attachment system 236 is shown in FIGS. 2 and 3 (FIG. 3 is a cross sectional view of the insert 220 taken along the line 3—3 of FIG. 2). As is shown in FIG. 2, the clothing attachment system 236 is located adjacent both the end edges 252 and the longitudinal sides 250 of the insert 220. The clothing attachment system 236 shown in FIG. 2 is joined to the waist feature 234 on the outer surface 240 of the insert 220.

As shown in greater detail in FIG. 3, this preferred embodiment of the clothing attachment system 236 comprises an adhesive attachment layer 370 and a protective release layer 372. The protective release layer 372 prevents contamination of the adhesive attachment layer 370 prior to the use of the insert 220. The adhesive attachment layer 370 is joined to the backsheet 226 in the first portion 268 of the elastic waist feature 234.

The adhesive attachment layer 370 can comprise a uniform continuous layer of adhesive, or an array of separate lines, spirals or spots of adhesive. If extensible adhesives are used, any of these patterns can be used. Whereas, if an inextensible adhesive is used, only intermittent patterns can be used so stretch can occur between points of attachment. A suitable extensible adhesive is an elastically extensible adhesive film known as 3M XPO-0-014 available from Minnesota Mining and Manufacturing Company of St. Paul, Minn. Suitable inextensible adhesives may be those adhesives specified as 0.6 mil pass available from Century Adhesive as product number A305-4, or from Anchor Continental, Inc., 3 Sigma Division of Covington, Ohio. Other adhesives as are known in the art may also be used. A particularly preferred adhesive attachment layer 370 will comprise a slot extruded elastically extensible adhesive film, such as Findley adhesive 198-338 supplied by Findley Adhesives of Wauwatosa, Wis.

Also as shown in FIG. 3, a preferred embodiment of the fit panel 238 comprises the topsheet 224, the backsheet 226 and an elastic member 330. Referring to FIGS. 2 and 3, the fit panel 238 extends longitudinally outwardly from the waist ends 262 of the containment assembly 222 to the waist edges of the fit panel 264 and laterally between the longitudinal sides 250 of the insert 220. In this preferred embodiment, the chassis edge 266 of a fit panel 238 is joined to a waist edge 262 of the containment assembly 222 and extends longitudinally outwardly to the waist edge of the fit panel 264.

As noted hereinabove, in preferred embodiments of the present invention at least a portion of both the topsheet 224 and the backsheet 226 have been subjected to some degree of mechanical stretching. In a particularly preferred embodiment of the fit panel 238, the topsheet 224 and the backsheet 226 have been directed through an incremental mechanical stretching system and joined to the elastic member 330 in order to form a "zero strain stretch laminate". As is shown in FIG. 3, the fit panel 238 has been provided with discrete regions of securement 378 wherein the topsheet 224 and the backsheet 226 are joined by means familiar to the art to the elastic member 330. Such "zero strain stretch laminates" are discussed in greater detail in U.S. Pat. No. 5,151,092 entitled "Absorbent Article With Dynamic Elastic Waist Feature Having A Predisposed Resilient Flexural Hinge" which issued to Kenneth B. Buell et al. on Sep. 29, 1992 which is included herein by reference. The fit panel 238 is shown in FIG. 3 in its relaxed state. In particular, the elastic member 330 is not stretched in this state. As a result, the mechanically stretched portions of the topsheet 224 and the backsheet 226 located between the regions of securement 378 form pleats 380.

Examples of materials suitable for use as an elastic member 330 include elastomeric films, elastomeric foams such as polyurethane foams or crosslinked natural rubber foams; formed elastic scrim; elastomeric films such as heat shrinkable elastic materials; and elastic strands made from rubber, Lycra®, or other materials. In a preferred embodiment the elastic member 330 comprises an elastomeric foam. Exemplary elastomeric foams which have been found suitable include: (a) crosslinked natural rubber foams preferably having a caliper of approximately 50 mils and a density of 13.3 pounds per cubic foot (0.214 g/cm$^3$), such as is available from Fullflex Inc. of Middletown, R.I.; or as available from Ludlow Composites Corporation of Freemont, Ohio; or (b) polyurethane foams having a caliper of approximately 80 mils and a density of approximately 26 pounds per cubic foot (0.033 g/cm$^3$) such as is available from Bridgestone of Yokohama, Japan and marketed under the tradename Bridgestone SG polyurethane foam; or as available from General Foam of Paramus, N.J. and marketed under the designation of Polyurethane Foam No. 40310. In a still more preferred embodiment, the elastic member 330 comprises an elastically extensible adhesive film such as Findley adhesive 198-338 supplied by Findley Adhesives of Wauwatosa, Wis.

Alternatively, the fit panel 238 can comprise a SELF laminate. In this case, a portion of the backsheet 226 is laminated to a portion of the topsheet using means well known to the art. The laminate is then provided with the network of regions of differing surface pathlength as described hereinabove to form a SELF laminate. The SELF laminate is elastically extensible such that it provides the necessary body contact force for a fit panel (the Young's modulus of the topsheet and the backsheet must be tailored to insure that the body contact force and the stress relaxation properties of the SELF laminate are within the ranges described hereinabove).

Figure 4:
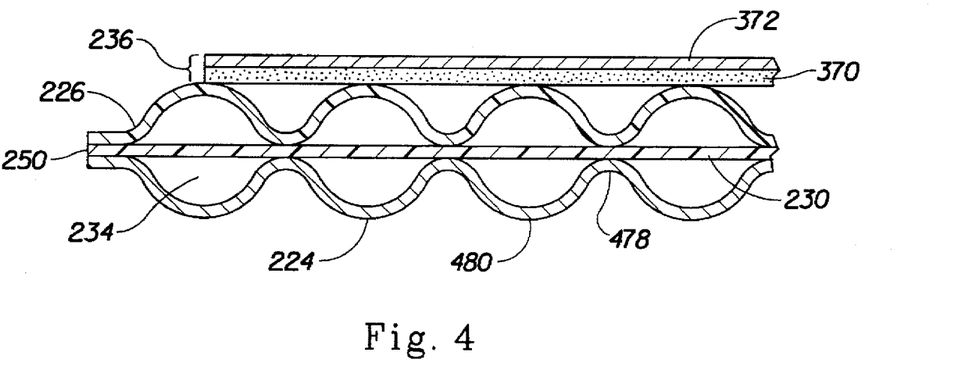
FIG. 4 is a fragmentary sectional view of the absorbent insert of FIG. 2 taken along section line 4—4 of FIG. 2.

Further, as shown in FIGS. 3 and 4, a preferred embodiment of the waist feature 234 comprises the topsheet 224, the backsheet 226 and an elastic member 330. Referring to FIG. 3, the elastic waist feature 234 extends longitudinally outwardly from the waist edge 264 of the fit panel to the end edges of the insert 252.

As shown in FIG. 4, the waist feature 234 is constructed similarly to the fit panel 238. That is, the waist feature comprises mechanically strained topsheet 224 and backsheet 226 with discrete regions of securement 478 joining (means not shown) them to the elastic member 330 to provide a "zero strain" stretch laminate. Means for providing these regions of securement are identical to those discussed hereinabove in reference to the fit panels 238. Also, the portions of the topsheet 224 and the backsheet 226 between the regions of securement 478 also form pleats 480 when the elastic waist feature 234 is in a relaxed state. Alternatively, the waist feature 234 can comprise a SELF laminate as described hereinabove.

The description of the preferred embodiment of the waist feature 234 hereinabove is not intended to limit the scope of the present invention solely to waist features comprising elastically extensible materials. Since the waistband of typical commercially available undergarments can elastically expand and contract to dynamically fit a wearer's waist, the waist feature of the present invention need only be stretchable. As used herein, the term "stretchable" refers to materials that are extensible when forces are applied to the material, and offer some resistance to extension.

Figure 5:
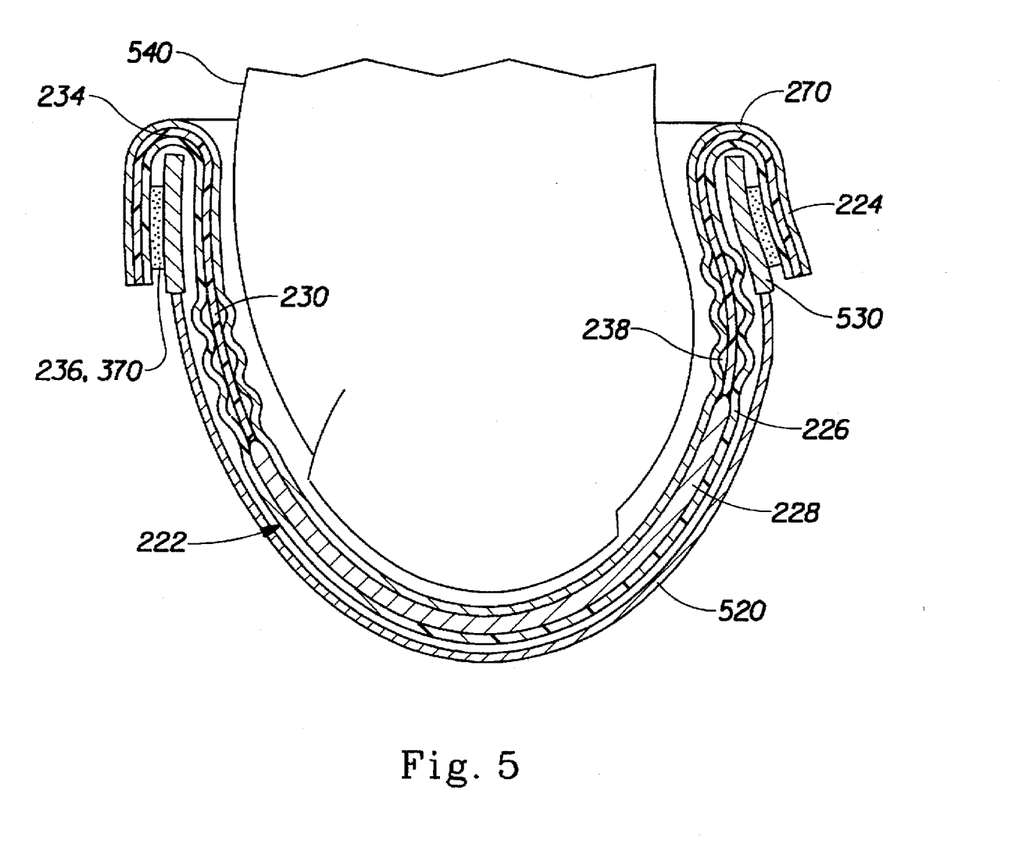
FIG. 5 is a partial coronal cross section showing the absorbent insert being worn.

The insert 220 may be worn as shown in FIG. 5. After the protective release layer 372 has been removed, the elastic waist feature 234 is folded about and attached to the outside of the waistband 530 of a wearer's 540 underwear 520 using the adhesive attachment layer 370. The wearer's legs are then inserted through the leg openings (not shown) of the underwear 520 and the underwear pulled up in the normal manner. By folding the waist feature 234 about and attaching it to the outside of the waistband 530, the waistband 530 becomes part of the support structure for the containment assembly 222. That is, the waistband distributes part of the body contact force reducing the stresses on the adhesive attachment layer resulting in more reliable attachment of the insert 220. As noted hereinabove, the longitudinal vector component of the elastic extensibility in the fit panel 238 provides the body contact force which helps insure good contact of the containment assembly 222 with the wearer 540 throughout the full range of wearer movement. Additionally, the lateral vector component of the elastic extensibility in the preferred waist feature 234 and the clothing attachment system 236 helps insure that the insert 220 not only adjusts to dimensional changes in the wearer's 540 waist but also that the insert 220 remains attached to the waistband 230 of the wearer's underwear 520.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for fitting about a wearer's body, the absorbent article having longitudinal and lateral centerlines, which respectively define a longitudinal and a lateral direction, the absorbent article comprising:

a containment assembly having first and second end edges, said containment assembly comprising a liquid pervious topsheet, a liquid impervious backsheet joined with said topsheet, and an absorbent core positioned intermediate said topsheet and said backsheet;

a first fit panel having a first waist edge and a first chassis edge longitudinally opposite said first waist edge, said first chassis edge being joined to said containment assembly adjacent said first end edge of said containment assembly, said first fit panel being elastically extensible with a vector component in the longitudinal direction, said elastic extensibility providing a body contact force;

a first waist feature being joined to said first fit panel adjacent said first waist edge, said first waist feature being elastically extensible with a vector component in the lateral direction; and a fastening system disposed on said first waist feature for maintaining lateral tension through at least a portion of said first waist feature.

2. The absorbent article of claim 1 wherein the absorbent article additionally comprises:

a second fit panel having a second waist edge and a second chassis edge longitudinally opposite said second waist edge, said second chassis edge being joined to said second end edge of said containment assembly, said second fit panel being elastically extensible with a vector component in the longitudinal direction, said elastic extensibility providing a body contact force;

a second waist feature being joined to said second fit panel adjacent said second waist edge, said second waist feature being elastically extensible with a vector component in the lateral direction; and a portion of said fastening system also being disposed on said second waist feature for maintaining lateral tension through at least a portion of said second waist feature.

3. The absorbent article of claim 2 wherein said second fit panel is elastically extensible to about 1.5 to 2 times the elastic extensibility of said first fit panel.

4. The absorbent article of claim 2 wherein the absorbent article is a disposable diaper and said fastening system comprises a dual tension fastening system.

5. The absorbent article of claim 2 wherein said first and second fit panels are elastically extensible with vector components in both the longitudinal and lateral directions.

6. The absorbent article of claim 2 wherein said first and second fit panels comprise a zero strain stretch laminate.

7. The absorbent article of claim 2 wherein said first and second fit panels comprise a structural elastic-like film web.

8. The absorbent article of claim 1 wherein said first fit panel has a body contact force of less than 200 grams when said first fit panel is extended from about 0.25 cm to about 5 cm.

9. An absorbent article for insertion into a user's undergarments and attachment thereto, the absorbent article having longitudinal and lateral centerlines respectively defining a longitudinal and a lateral direction, the absorbent article comprising:

a containment assembly having first and second end edges, said containment assembly comprising a liquid pervious topsheet, a liquid impervious backsheet joined with said topsheet, and an absorbent core positioned intermediate said topsheet and said backsheet;

a first fit panel having a first waist edge and a first chassis edge longitudinally opposite said first waist edge, said first chassis edge being joined to said containment assembly adjacent said first end edge of said containment assembly, said first fit panel being elastically extensible with a vector component in the longitudinal direction, said elastic extensibility providing a body contact force;

a first waist feature being joined to said first fit panel adjacent said first waist edge; and a clothing attachment system disposed on said first waist feature for attaching the absorbent article to the undergarment.

10. The absorbent article of claim 9 wherein the absorbent article additionally comprises:

a second fit panel having a second waist edge and a second chassis edge longitudinally opposite said second waist edge, said second chassis edge being joined to said second end edge of said containment assembly, said second fit panel being elastically extensible with a vector component in the longitudinal direction, said elastic extensibility providing a body contact force;

a second waist feature being joined to said second fit panel adjacent said second waist edge; and a portion of said clothing attachment system also being disposed on said second waist feature for attaching the absorbent article to the undergarment.

11. The absorbent article of claim 10 wherein said first and second waist features are elastically extensible with a vector component in the lateral direction.

12. The absorbent article of claim 9 wherein said first fit panel is elastically extensible with vector components in both the longitudinal and lateral directions.

13. The absorbent article of claim 9 wherein said first fit panel comprises a zero strain stretch laminate.

14. The absorbent article of claim 9 wherein said first fit panel comprises a structural elastic-like film web.

15. The absorbent article of claim 9 wherein said first fit panel has a body contact force of less than 200 grams when said first fit panel is extended from about 0.25 cm to about 5 cm.

16. The absorbent article of claim 10 wherein said clothing attachment system comprises an adhesive area.

17. The absorbent article of claim 16 wherein said adhesive area comprises an extensible, pressure sensitive adhesive.

18. The absorbent article of claim 10 wherein said clothing attachment system comprises a hook fastening material.

19. An absorbent article which can be inserted into a user's undergarments and attached adjacent the waistband of the undergarment, the absorbent article having longitudinal and lateral centerlines which respectively define a longitudinal and a lateral direction, the absorbent article comprising:

a containment assembly having first and second end edges, said containment assembly comprising a liquid pervious topsheet, a liquid impervious backsheet joined with said topsheet, and an absorbent core positioned intermediate said topsheet and said backsheet;

a first fit panel having a first waist edge and a first chassis edge longitudinally opposite said first waist edge, said first chassis edge being joined to said first end edge of said containment assembly, said first fit panel being elastically extensible with a vector component in the longitudinal direction;

a second fit panel having a second waist edge and a second chassis edge longitudinally opposite said second waist edge, said second chassis edge being joined to said second end edge of said containment assembly, said second fit panel having an elastic extensibility about 1.5 to 2 times the elastic extensibility of said first fit panel, said second fit panel being elastically extensible with a vector component in the longitudinal direction;

a first waist feature being joined to and extending longitudinally outwardly from said first waist edge of said first fit panel, said first waist feature being stretchable with a vector component in the lateral direction;

a second waist feature being joined to and extending longitudinally outwardly from said second waist edge of said second fit panel, said second waist feature being stretchable with a vector component in the lateral direction; and a clothing attachment system disposed on said first waist feature and said second waist feature wherein said first waist feature and said second waist feature can be attached adjacent the waistband of the undergarment.

20. The absorbent article of claim 19 wherein said clothing attachment system comprises an adhesive.

21. The absorbent article of claim 20 wherein said adhesive is an elastically extensible, pressure sensitive adhesive.

22. The absorbent article of claim 19 wherein said clothing attachment system comprises a hook fastening material.

23. An absorbent pant, the absorbent pant having longitudinal and lateral centerlines which respectively define a longitudinal and a lateral direction, the absorbent pant comprising:

a containment assembly having first and second end edges, said containment assembly comprising a liquid pervious topsheet, a liquid impervious backsheet joined with said topsheet, and an absorbent core positioned intermediate said topsheet and said backsheet;

a first fit panel having longitudinal edges, a first waist edge, and a first chassis edge longitudinally opposite said first waist edge, said first chassis edge being joined to said first end edge of said containment assembly, said first fit panel being elastically extensible with a vector component in the longitudinal direction;

a second fit panel having longitudinal edges, a second waist edge, and a second chassis edge longitudinally opposite said second end edge, said second chassis edge being joined to said second end edge of said containment assembly, said second fit panel having an elastic extensibility about 1.5 to 2 times the elastic extensibility of said first fit panel, said second fit panel being elastically extensible with a vector component in the longitudinal direction;

a first waist feature having transverse edges and first and second longitudinal edges, one of said transverse edges of said first waist feature being joined to said first waist edge of said first fit panel with said longitudinal edges of said first waist feature being laterally outboard of said longitudinal edges of first fit panel, said first waist feature being elastically extensible with a vector component in the lateral direction;

a second waist feature having transverse edges and first and second longitudinal edges, one of said transverse edges of said second waist feature being joined to said second waist edge of said second fit panel with said longitudinal edges of said second waist feature being laterally outboard of said longitudinal edges of said second fit panel, said second waist feature being elastically extensible with a vector component in the lateral direction; and seams joining said first longitudinal edge of said first waist feature with said first longitudinal edge of said second waist feature and said second longitudinal edge of said first waist feature with said second longitudinal edge of said second waist feature.

* * * * *

UNITED STATES PATENT AND TRADEMARK OFFICE
CERTIFICATE OF CORRECTION

PATENT NO.    : 5,690,627                                        Page 1 of 1
DATED         : November 25, 1997
INVENTOR(S)   : Sandra H. Clear et al.

It is certified that error appears in the above-identified patent and that said Letters Patent is hereby corrected as shown below:

<u>Column 4,</u>
Line 2, "alter" should read -- after --.

<u>Column 5,</u>
Line 13, "coveting" should read -- covering --.

Signed and Sealed this

Sixteenth Day of July, 2002

*Attest:*

*Attesting Officer*

JAMES E. ROGAN
*Director of the United States Patent and Trademark Office*